United States Patent
Fukuda

(10) Patent No.: US 7,599,066 B2
(45) Date of Patent: Oct. 6, 2009

(54) LOCALIZED PLASMON RESONANCE SENSOR

(75) Inventor: Koichi Fukuda, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 325 days.

(21) Appl. No.: 11/441,029

(22) Filed: May 26, 2006

(65) Prior Publication Data
US 2006/0281170 A1 Dec. 14, 2006

(30) Foreign Application Priority Data
Jun. 1, 2005 (JP) ............... 2005-161853

(51) Int. Cl.
*G01N 21/55* (2006.01)
(52) U.S. Cl. ............ 356/445; 356/234; 356/301; 435/4; 435/15; 435/335
(58) Field of Classification Search ......... 356/437–445, 356/128, 301, 317; 435/4, 15, 287.2, 335, 435/24
See application file for complete search history.

(56) References Cited

U.S. PATENT DOCUMENTS

| 6,344,272 | B1 | 2/2002 | Oldenburg et al. | 428/403 |
| 7,015,471 | B2 * | 3/2006 | Franzen et al. | 435/4 |
| 2006/0286684 | A1 * | 12/2006 | Brennan et al. | 435/287.2 |

FOREIGN PATENT DOCUMENTS

| JP | 2000-356587 | 12/2000 |
| JP | 2003-247936 | 9/2003 |
| WO | 01/06257 | 1/2001 |

OTHER PUBLICATIONS

J. Gonzalo, et al., "Morphological and interaction effects on the surface plasmon resonance of metal nanoparticles", Journal of Physics, vol. 15, No. 42, 2003, pp. S3001-S3010.
S. A. Kalele, et al, "Optical detection of antibody using silica-silver core-shell particles", Chemical Physics Letters, vol. 404, 2005, pp. 136-141.
Corey Radloff, et al., "Plasmonic Properties of Concentric Nanoshells", Nano Letters, vol. 4, No. 7, 2004, pp. 1323-1327.
Duncan S. Sutherland, et al., "Optical Properties of Shaped Gold Nanoparticles", 7th International Conference on Nanometer-Scale Science and Technology and 21st European Conference on Surface Science, Lund Univ., Sweden, 2002, 2 pages.
Felicia Tam, et al., "Geometrical Parameters Controlling Sensitivity of Nanoshell Plasmon Resonances to Changes in Dielectric Environment", Journal of Physical Chemistry B, vol. 108, No. 45, 2004, pp. 17290-17294.
Jian Zhu, et al., "Fluorescence Spectrum Characteristics of Gold Nanorods", Chinese Physics Letters, vol. 21, No. 3, 2004, pp. 559-561.

* cited by examiner

Primary Examiner—Gregory J Toatley, Jr.
Assistant Examiner—Iyabo S Alli
(74) Attorney, Agent, or Firm—Fitzpatrick, Cella, Harper & Scinto

(57) ABSTRACT

A localized plasmon resonance sensor for detecting a change in optical constant uses a structure including metal. In a response spectrum with respect to light incident on the structure, there are at least two resonance peaks including at least one resonance peak shifted to a longer wavelength side and at least another peak shifted to a shorter wavelength side, by the change in optical constant.

14 Claims, 4 Drawing Sheets

LOCALIZED PLASMON RESONANCE SENSOR

FIELD OF THE INVENTION AND RELATED ART

The present invention relates to a localized plasmon resonance sensor for detecting a chemical substance, a chemical reaction, a living body, genetic information, etc. The present invention also relates to a sensing method using the localized plasmon resonance sensor and a particle for use with the localized plasmon resonance sensor.

In recent years, as a sensor capable of detecting the chemical substance, the chemical reaction, the living body, the genetic information, etc., a localized plasmon resonance sensor has been developed. The localized plasmon resonance sensor utilizes a localized plasmon resonance phenomenon caused by an interaction between conduction electron and light in metal. More specifically, the localized plasmon resonance sensor detects a change of a minute area of several to several tens of nm in a neighborhood of a surface of a metal structure so as to permit detection of the chemical substance, the chemical reaction, the living body, the genetic information, etc.

Particularly, in the medical field, an antigen-antibody reaction detection sensor using metal nanoparticles modified with an antigen or an antibody has been advanced. For example, Japanese Laid-Open Patent Application (NP-A) 2000-356587 has proposed a localized plasmon resonance sensor using metal fine particles. The localized plasmon resonance sensor is capable of detecting a change of a medium in the neighborhood of the metal fine particles by irradiating a substrate, on which the metal fine particles are fixed, with light to measure an absorbance of light transmitted through the metal fine particles by means of a spectrometer.

Herein, an embodiment of the localized plasmon resonance sensor and a detection method using the localized plasmon resonance sensor will be briefly described with reference to FIG. 1.

In FIG. 1, a curve 501a represents an absorption spectrum at the time when light is caused to enter spherical gold (Au) nanoparticles 101 having a radius of 20 nm placed in a medium having a refractive index of 1.333. From the curve 501a, it is found that a localized plasmon resonance peak is present at a wavelength of approximately 525 nm. Localized plasmon resonance is a phenomenon occurring in the case where there is an interface between metal and dielectric material. In this case, a resonance condition varies depending on a change in optical constant such as refractive indices of the metal and the dielectric material in the neighborhood of the interface. Referring again to FIG. 1, curves 501b and 501c represent adsorption spectra in the case where the spherical gold nanoparticles 101 are coated with a film 104 of protein having a refractive index of 1.4 in thicknesses of 10 nm and 20 nm, respectively. From these curves 501b and 501c, it is found that the resonance peak is shifted to a longer wavelength with an increase in refractive index at a peripheral portion due to an increase in thickness of the protein film, thus resulting in a change in absorbance (a red shift of the resonance peak). The localized plasmon resonance sensor is capable of detection of the chemical substance, the chemical reaction, the living body, the genetic information, or the like by observing the change in resonance peak, As the metal structure used for the localized plasmon resonance sensor, in addition to the spherical metal particles, utilization of metal particles having other shapes such as ellipsoid, circular cylinder, circular plate, and polygon. Further, e.g., U.S. Pat. No. 6,344,272 has proposed a localized plasmon resonance sensor using a complicated metal structure such as a multi-layer shell structure.

The above described localized plasmon resonance sensors are used to realize a sensor function by detecting a change in resonance peak due to a change in optical constant at a peripheral portion of the metal structure. In order to enhance a sensitivity of the localized plasmon resonance sensor, it is necessary to increase an amount of shift to a longer wavelength (red shift) of a resonance frequency with respect to a line width (half-value width) of localized plasmon resonance peak.

However, in the localized plasmon resonance sensor proposed above in JP-A 2000-356587, in the case of detecting an antigen-antibody reaction, the following problem has arisen.

More specifically, a difference in resonance frequency and resonance intensity between the resonance spectrum 501b in a state of presence of only an antibody around the god nanoparticles and the resonance spectrum 501c in a state of presence of an antigen in addition to the antibody around the gold nanoparticles is slight. For this reason, it is difficult to improve an SN ratio of the sensor, so that the resultant localized plasmon resonance sensor is liable to be adversely affected by a production error of the metal particles and a measurement error during detection.

Further, U.S. Pat. No. 6,344,272 described above has proposed such a complicated nanosize metal structure that the red shift of the resonance peak is increased in order to improve the SN ratio by localizing the resonance frequency of the localized plasmon resonance on a long wavelength side. However, in an actual localized plasmon resonance sensor, a group of metal structure is used, so that a large number of different localized plasmon resonance spectra are copresent in mixture due to an irregularity in structure resulting from the production error. As a result, the resultant localized plasmon resonance sensor has accompanied with such a problem that the line width (half-value width) of the localized plasmon resonance spectra as that of the group of metal structure is broadened. Particularly, as the metal structure has a larger red shift of the resonance peak, an irregularity in resonance frequency due to the irregularity in structure is larger. As a result, the line width (half-value width) of the entire resonance spectrum is liable to be considerably broadened, so that it is difficult to improve the SN ratio of the localized plasmon resonance sensor, which his also liable to be adversely affected by the production error of the sensor and the measurement error during detection.

SUMMARY OF THE INVENTION

An object of the present invention is to provide a localized plasmon resonance sensor having solved the above described problems.

A specific object of the present invention is to provide a localized plasmon resonance sensor capable of detection with high sensitivity.

Another object of the present invention is to provide a sensing method using the localized plasmon resonance sensor.

A further object of the present invention is to provide a particle for use with the localized plasmon resonance sensor.

According to an aspect of the present invention, there is provided a localized plasmon resonance sensor for detecting a change in optical constant using a structure comprising metal, the improvement residing in that in a response spectrum with respect to light incident on the structure, there are at least two resonance peaks including at least one resonance peak shifted to a longer wavelength side and at least another peak shifted to a shorter wavelength side, by the change in optical constant.

According to another aspect of the present invention, there is provided a sensing method, comprising: preparing a structure comprising metal; and preparing a localized plasmon resonance sensor for detecting a change in optical constant; the improvement residing in that in a response spectrum with respect to light incident on said structure, there are at least two resonance peaks including at least one resonance peak shifted to a longer wavelength side and at least another peak shifted to a shorter wavelength side, by the change in optical constant.

According to a further aspect of the present invention, there is provided a particle for use with a localized plasmon resonance sensor for detecting a change in optical constant, the improvement residing in that in a response spectrum with respect to light incident on said structure, there are at least two resonance peaks including at least one resonance peak shifted to a longer wavelength side and at least another peak shifted to a shorter wavelength side, by the change in optical constant.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 2A to 2D are schematic views for illustrating a principle of a localized plasmon resonance sensor according to the present invention, in which FIG. 2A is a graph showing a relationship between a wavelength of incident light and a dependency of silver film thickness, of absorption spectrum of silver nanoparticles having a shell structure, FIG. 2B includes schematic views of absorption spectrum of the silver nanoparticles having the shell structure, FIG. 2C is a graph for illustrating a shift of resonance peak of absorption spectrum with respect to a change in refractive index in the neighborhood of a surface of silver nanoparticle having the shell structure, and FIG. 2D is a graph for illustrating a change in absorption spectrum with respect to a change in refractive index in the neighborhood of a surface of silver nanoparticle having the shell structure (silver film thickness: 1.26 nm).

FIGS. 3A and 3B are schematic views for illustrating a constitution of a plasmon resonance sensor apparatus in an embodiment of the present invention, in which FIG. 3A is a schematic side view showing the constitution of the sensor apparatus and FIG. 3B is a front view showing a flow path of the sensor apparatus shown in FIG. 3A.

DETAILED DESCRIPTION OF THE PREFERRED EMBODIMENTS

The present invention has been accomplished on the basis of the following findings.

As a result of study by the present inventor, it has been found that there is a metal structure exhibiting a pair of a resonance peak which is shifted to a longer wavelength (red shifted) and a resonance peak which is shifted to a shorter wavelength (blue shifted) in an absorption spectrum when metal nanoparticles having a shell structure, prepared as a structure comprising metal (i.e., metal structure) used for a localized plasmon resonance sensor, are changed in structure.

In an ordinary localized plasmon resonance sensor, the pair of the resonance peak which is red shifted and the resonance peak which is blue shifted is not used for the sensor.

In the present invention, a change of the pair of the red shifted resonance peak and the blue shift resonance peak in the absorption spectrum is detected and used for the localized plasmon resonance sensor, so that it is possible to improve an SN ratio of the sensor. As a result, it is possible to realize detection with high sensitivity.

Such a principle of the present invention will be described with reference to FIGS. 2A to 2D showing one analysis embodiment of resonance peak.

Figure 1:
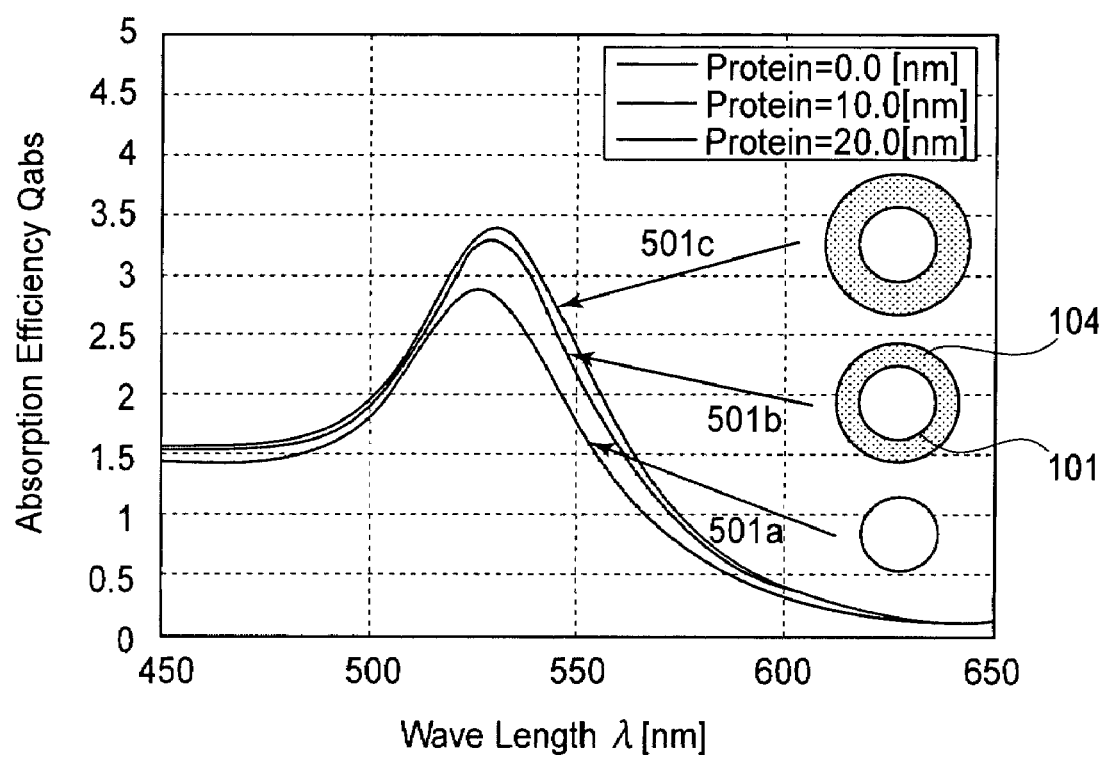
FIG. 1 is a schematic graph for illustrating a principle of a localized plasmon resonance sensor.
Figure 2A:
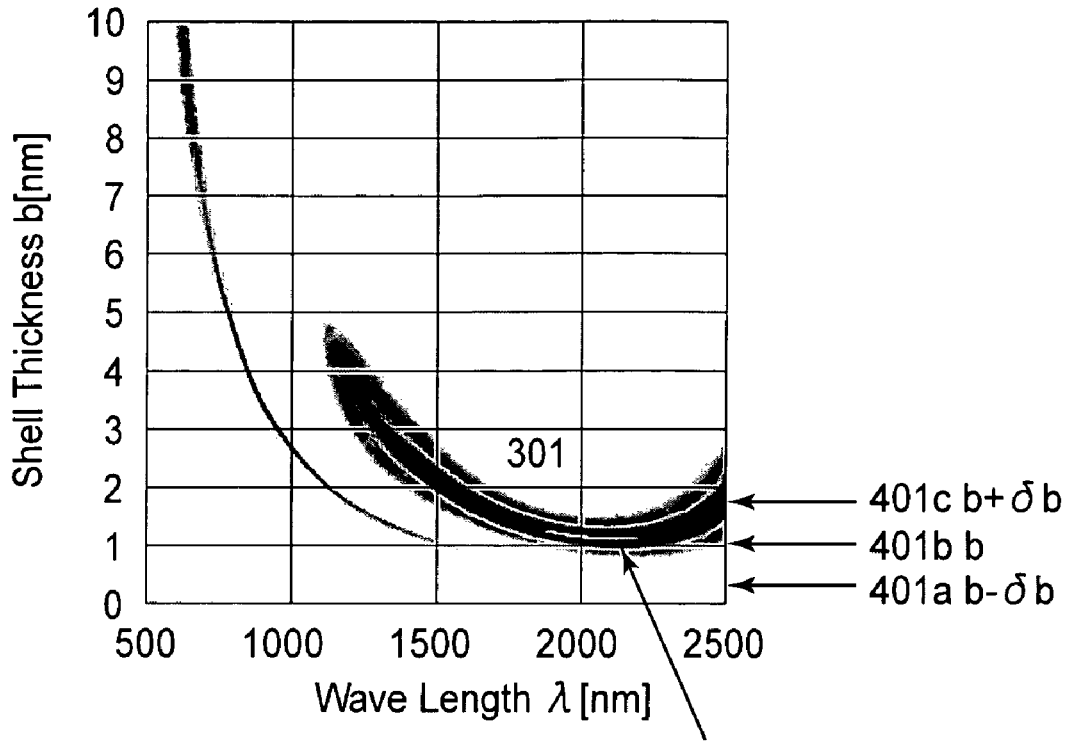

FIG. 2A is a graph in which absorption spectra of silver nanoparticles each having a shell structure comprising a spherical silica core having a radius of 80 nm and a silver film having a thickness b coated on the silica core are indicated as a function of a $\delta$ and the silver film thickness b. In the graph, an ordinate represents the silver film thickness b (nm) and an abscissa represents the wavelength $\delta$ (nm) of incident light.

In FIG. 2A, a reference numeral 301 represents an area in which there is a localized plasmon resonance peak. A reference numeral 302 represents an area, in the neighborhood of a wavelength $\delta$ of approximately 2050 nm and a silver film thickness b of approximately 1.2 nm, two resonance peaks are degenerated into one resonance peak (hereinafter referred to as a "degeneracy area").

Figure 2B:
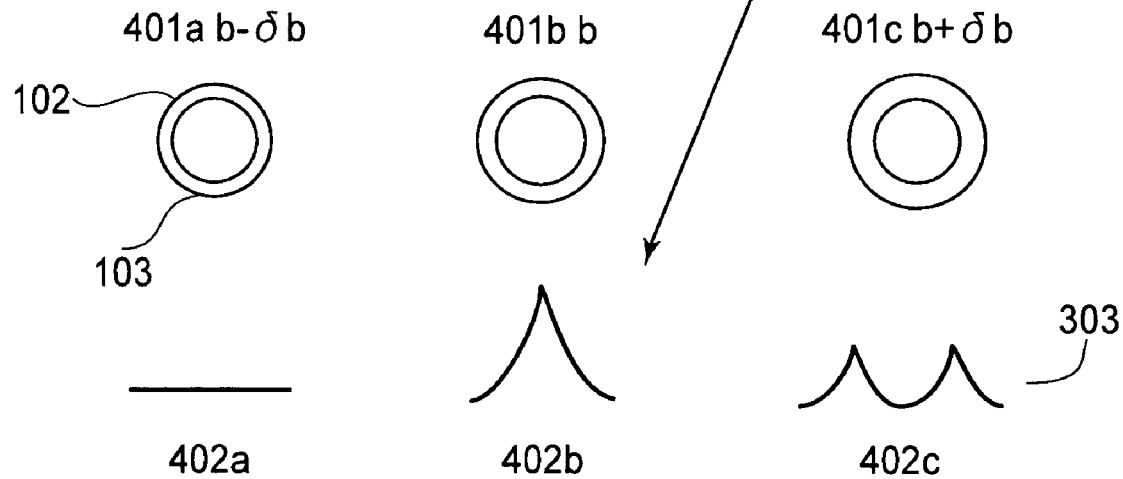

Here, areas close to the degeneracy area are studied in more detail. As a result, in an area of silver film thicknesses of 1.1 nm of 0 nm thinner than the silver film thickness of 1.2 nm of the silver nanoparticles allowing presence of the degeneracy area, as apparent from FIG. 2A, localized plasmon resonance disappears. On the other hand, in an area of silver film thickness of 1.3 nm to 2.0 nm thicker than the silver film thickness of 1.2 nm, one localized plasmon resonance peak within and in the neighborhood of the degeneracy area is separated into two resonance peaks and gradually extended with an increasing silver film thickness. The results thereof are schematically shown in FIG. 2B.

Figure 2C:
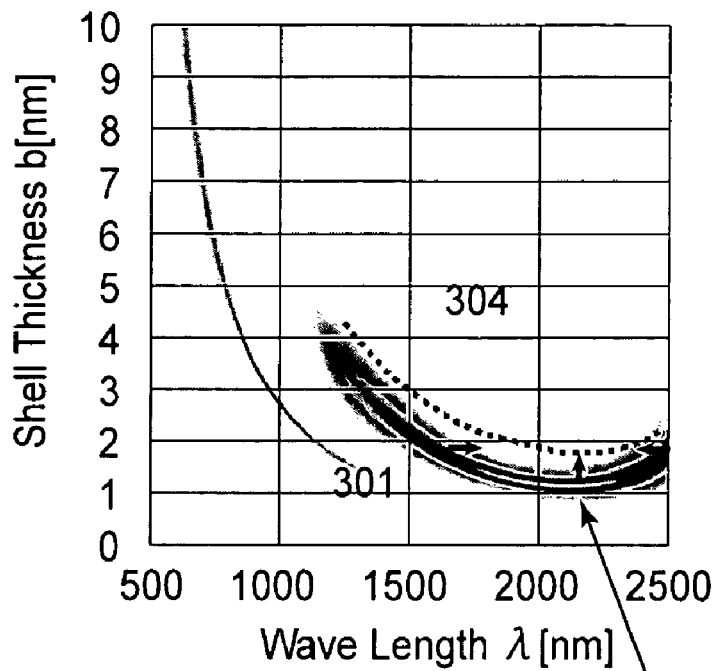

Further, a result of study on a change in localized plasmon resonance peak in the neighborhood of the degeneracy area, as indicated by a reference numeral 304 in FIG. 2C, it has been clarified that the resonance peaks are shifted toward a direction of a larger silver film thickness as a whole with an increase in refractive index of an ambient medium. Accordingly, it is understand that when the degeneracy of the resonance peaks is released or removed to cause separation into two resonance peaks, the two resonance peaks includes one resonance peak causing red shift (shift to a longer wavelength) and the other resonance peak causing blue shift (shift to a shorter wavelength). As a result, it has been confirmed that the resonance peak causing red shift and the resonance peak causing blue shift are present as a pair in the neighborhood of the above described degeneracy area.

Figure 2D:
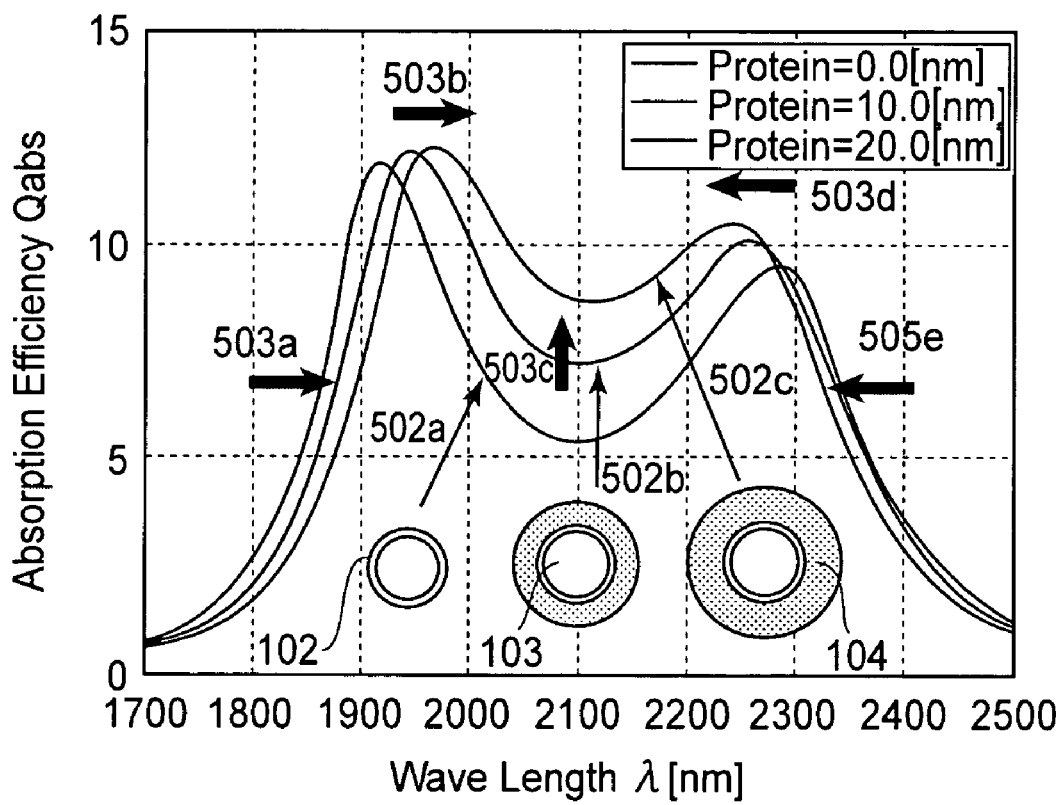

FIG. 2D shows three curves 502a, 502b, and 502c each representing an absorption spectrum. The curve 502a represents an absorption spectrum when a silver nanoparticle having a shell structure prepared by coating a spherical silica core 103 having a radius of 20 nm with a 1.27 nm-thick silver film 102 is placed in a medium having a refractive index of 1.333 and light is caused to enter the silver nanoparticle. From the curve 502a, it is understood that there are two localized plasmon resonance peaks. The curves 502b and 502c represent adsorption spectra in the cases where the above silver nanoparticle is coated with protein films 104, having a refractive index of 1.4, in thicknesses of 10 nm (502b) and 20 nm (502c), respectively. Further, in FIG. 2D, resonance peaks in a wavelength range of 1900-2000 nm cause red shift (503b)

and resonance peaks in a wavelength of 2200-2300 nm cause blue shift (503c). Further, from FIG. 2D, it is understood that a characteristic change in absorption spectrum is caused to occur in the case where a red shifting resonance peak and a blue shifting resonance peak are copresent in the above described absorption spectrum of the silver nanoparticles.

Here, for convenience of explanation, in the above described absorption spectrum, the resonance peak located on the shorter wavelength side is referred to as a "resonance peak 1" and the resonance peak located on the longer wavelength side is referred to as a "resonance peak 2".

In the case where the resonance peak 1 is red shifted (shifted to a longer wavelength side) and the resonance peak 2 is blue shifted (shifted to a shorter wavelength side), the absorption spectrum described above causes a first change such that an absorption edge on the shorter wavelength side of the resonance peak 1 is red shifted (503a in FIG. 2D). As a second change, a resonance frequency of the resonance peak 1 is red shifted (503b in FIG. 2D). As a third change, a bottom of absorption spectrum between the resonance peak 1 and the resonance peak 2 moves upward (503c in FIG. 2D). As a fourth change, a resonance frequency of the resonance peak 2 is blue shifted (503d in FIG. 2D) As a fifth change, an absorption edge on the longer wavelength side of the resonance peak 2 is blue shifted (503e in FIG. 2D).

In the case where the resonance peak 1 is blue shifted and the resonance peak 2 is red shifted, the absorption spectrum described above causes a first change to a fifth change in opposite directions to the arrows 503a to 503e. More specifically, as the first change, an absorption edge on the shorter wavelength side of the resonance peak 1 is blue shifted (an opposite direction to 503a in FIG. 2D). As the second change, a resonance frequency of the resonance peak 1 is blue shifted (an opposite direction to 503b in FIG. 2D). As the third change, a bottom of absorption spectrum between the resonance peak 1 and the resonance peak 2 moves downward (an opposite direction to 503c in FIG. 2D). As the fourth change, a resonance frequency of the resonance peak 2 is red shifted (an opposite direction to 503d in FIG. 2D). As the fifth change, an absorption edge on the longer wavelength side of the resonance peak 2 is red shifted (an opposite direction to 503e in FIG. 2D).

Further, it has been clarified that the bottom portion of the absorption spectrum between the resonance peak 1 and the resonance peak 2 is present in the neighborhood of an intermediate position between the resonance peak 1 and the resonance peak 2 and is characterized in that its position is not largely changed corresponding wavelength with respect to the change in silver film thickness.

The above described features of the absorption spectra also apply to adsorption spectra of a group of shell-structured silver nanoparticles having a silver film thickness distribution ranging from approximately 1.2 nm to approximately 3.0 nm larger than the silver film thickness of approximately 1.2 nm allowing presence of the degeneracy area. More specifically, also in this case, it is understood that the absorption spectra are characterized by the above described first to fifth changes in the directions of the arrows 503a-503e and in the opposite directions to the arrows 503a-503e. Accordingly, in the case where in the changes of the above described absorption spectra, an opposite change is caused to occur with respect to any of the first to fifth changes, it is understood that there is a high probability of an occurrence of detection error.

Based on the results of the above described study a localized plasmon resonance sensor is constituted by using a group of silver nanoparticles prepared to have such a shell structure that a silver film thickness distribution ranges from approximately 1.2 nm to approximately 3.0 nm larger than the silver film thickness allowing presence of the above described degeneracy area. Further, any of or a combination of a plurality of the first change to the fifth change described above is measured to detect whether or not the change is caused to occur. By performing such an operation, it has been confirmed that it is possible to improve an SN ratio and a detection sensitivity of the localized plasmon resonance sensor.

The above described embodiment is merely one analysis embodiment for the principle of the localized plasmon resonance sensor according to the present invention, so that the present invention is not limited thereto. The localized plasmon resonance sensor of the present invention detects a change in optical constant by means of the metal structure and is characterized in that the response spectrum with respect to light incident on the metal structure has at leas two resonance peaks. At least one of the at least two resonance peaks is shifted to the longer wavelength side (red shifted) due to the change in optical constant, and at least another resonance peak is shifted to the shorter wavelength side (blue shifted) due to the change in optical constant. In the present invention, it is possible to use any type of a localized plasmon resonance sensor so long as the localized plasmon resonance sensor has the above described characteristic features.

In the case of spherically symmetric shell-structured nanoparticles, a localized plasmon resonance condition is represented by formulas (relationship) shown below. More specifically, a dielectric constant of a core portion as a dielectric member is taken as $\varepsilon_{core}$, a dielectric constant of a shell portion as metal is taken as $\varepsilon_{metal}$, a volume ratio of the core portion to the entire volume of nanoparticles is taken as f, and a dielectric constant of a solvent is taken as $\varepsilon_{medium}$. By using quasi-electrostatic field approximation, the localized plasmon resonance condition is represented by Formula 1 shown below, and a localized plasmon resonance frequency $\omega_{LPR}$ is represented by Formula 2 shown below. Further, in the spherically symmetric shell-structured nanoparticles, coefficients $\alpha$ and $\beta$ are represented by Formulas 3 and 4, respectively.

$$\varepsilon_{metal}(\omega_{LPR})^2 + 2\alpha\varepsilon_{metal}(\omega_{LPR}) + \beta = 0, \quad \text{Formula 1}$$

$$\varepsilon_{metal}(\omega_{LPR}) = -\alpha \pm \sqrt{\alpha^2 - \beta}, \quad \text{Formula 2}$$

$$\alpha = \frac{\varepsilon_{core} + 4\varepsilon_{medium} + 2f\varepsilon_{core} + 2f\varepsilon_{medium}}{4(1-f)}, \quad \text{Formula 3}$$

$$\beta = \varepsilon_{core}\varepsilon_{medium}, \quad \text{Formula 4}$$

With respect to ordinary spheroid-type shell structure, polyhedron-type shell structure, cylinder-type shell structure, semisphere-type shell structure, and disc-type structure, it is possible to gradually deform the spherically symmetric shell-structured nanoparticles. It can be considered that the coefficients $\alpha$ and $\beta$ vary depending on the change in associated structure.

From the Formula 1 for the localized plasmon resonance condition, it is possible to estimate a change $\delta\omega_{LPR}$ of the localized plasmon resonance frequency with respect to a change $\delta\varepsilon_{medium}$ of the solvent by the following Formula 5:

$$\frac{\partial \varepsilon_{metal}}{\partial \omega}\delta\omega_{LPR} = \left[\frac{-\frac{\partial \alpha}{\partial \varepsilon_{medium}} \pm \frac{1}{2\sqrt{\alpha^2 - \beta}}}{\left(2\alpha\frac{\partial \alpha}{\partial \varepsilon_{medium}} - \frac{\partial \beta}{\partial \varepsilon_{medium}}\right)}\right]\delta\varepsilon_{medium},$$

In the case where Formula 6 shown below is satisfied, there are two localized plasmon resonance peak pairs. Further, Formula 7 shown below is satisfied, an absolute value of the second term of the right-hand side of Formula 5 is larger than an absolute value of the first term, so that one causes red shift and the other causes blue shift.

$$\sqrt{\alpha^2 - \beta} > 0,$$ Formula 6

$$\sqrt{\alpha^2 - \beta} \ll 1.$$ Formula 7

Formula 7 is a condition showing presence in the neighborhood of the degeneracy area of the localized plasmon resonance. Accordingly, it is found that when Formulas 6 and 7 are satisfied, the nanoparticle structure has two localized plasmon resonance peaks including a peak causing red shift and a peak causing blue shift with respect to the change in solvent.

Further, in the present invention, the nanoparticle structure may satisfy Formulas 6 and 7 and a localized plasmon resonance condition represented by a quadratic equation, with respect to complex dielectric constant of metal, similar to Formula 1.

In the above described analysis embodiment, as the optical constant, the refractive index is used. However, in the present invention, it is also possible to use any of or a combination of a plurality of the refractive index, a dielectric constant, and a magnetic permeability.

The change in optical constant is determined by the change in thickness of the protein film in the above described analysis embodiment. The change in optical constant may also be determined by any one of or a combination of a plurality of a chemical reaction, a physical interaction, an antigen-antibody reaction, and a change in temperature.

In the analysis embodiment described above, as the response spectrum with respect to incident light, the absorption spectrum is used but the present invention is not limited thereto. More specifically, examples of the response spectrum may include a transmission spectrum, a reflection spectrum, a quenching spectrum, a scattering spectrum, and an expansion component and a polarization component during expansion of these spectra in respective characteristic modes.

The metal structure in the analysis embodiment has the shell structure of the silver nanoparticles but may also have such a structure that the metal structure has at least two interfaces between metal and a dielectric material and localized plasmon resonances at respective interfaces are correlated with each other. In this case, the metal structure may have a multi-layer shell structure. In the multi-layer shell structure, each layer may have, as an interface shape, not only a concentric circular shape but also a spheroidal shape, a polygonal shape, modified shapes of these, and combinations of a plurality of these. Further, the each layer of the multi-layer shell structure may be configured to be not only completely closed but also of a multi-layer semisphere type, a multi-layer circular plate type, modified types of these, and combinations of a plurality of these.

In the metal structure, the metal is not restricted to a single metal but may also be such an alloy of a plurality of species of metals that a composition thereof is continuously or discontinuously changed.

In the present invention, the metal structure of the localized plasmon resonance sensor may be disposed in a path in which a fluid is moved or in the neighborhood of an area in which a width of the path is narrowed in the path and may be configured so that the above described optical condition (optical constant) is changed depending on a solution and/or a solute moving within the path and information on a substance and/or a state in the path is measured or detected by a status of the response spectrum with respect to the light incident on the sensor. Further, the metal structure may be modified with an antigen or an antibody at a peripheral portion thereof.

Hereinbelow, the present invention will be described move specifically based on an embodiment but is not limited thereto.

In this embodiment, a localized plasmon resonance sensor apparatus is prepared by employing the above described constitution.

Figure 3A:
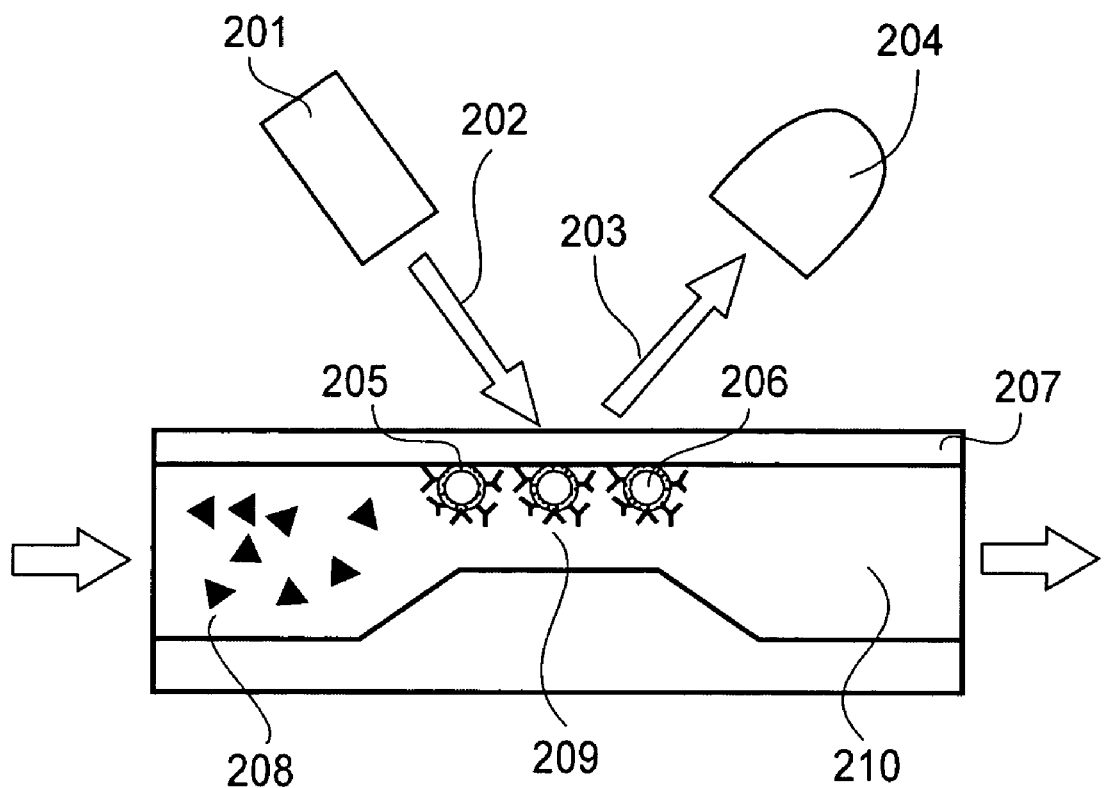
Figure 3B:
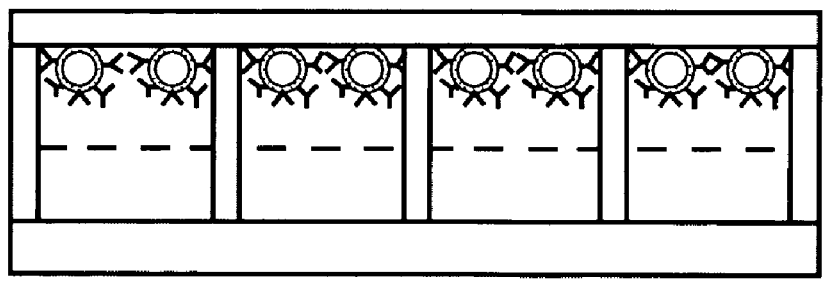

FIGS. 3A and 3B show the localized plasmon resonance sensor apparatus of this embodiment, wherein FIG. 3A is a schematic side view of the sensor apparatus, and FIG. 3B is a schematic front view thereof showing a path.

In these figures, the sensor apparatus includes a light source 201, incident light 202, reflected light 203, a light detector 204, silver 204 coated around spherical silica, a dielectric material 206 formed of the spherical silica, a glass substrate 207, an antigen 208, an antibody 209, and a micropath(microchannel) 210.

In this embodiment, in order to prepare a group of silver nanoparticles having a shell structure used for a localized plasmon resonance sensor, first of all, a plurality of spherical silica particles 206 having a radius of 80 nm is prepared. After the preparation of the silica particles 206, these particles may desirably be classified so as to have an error in radius within ±5 nm.

Next, the spherical silica particles 206 are surface-coated with the silver 205 so as to have an average of silver film thickness distribution of 1.2-3.0 nm, preferably 1.21-2.0 nm, which is somewhat larger than the silver film thickness of 1.2 nm allowing the presence of the degeneracy area. In this embodiment, the coating is performed with only silver but may also be performed with another metal or alloy. The coating may further be performed with a plurality of metals in multi-layers.

In this embodiment, the thus-prepared silver nanoparticles having the shell structure are used to constitute a group thereof which is used to prepare a localized plasmon resonance sensor apparatus. More specifically, the group of silver nanoparticles is modified with the antibody 209 and fixed on the glass substrate 207. Further, the micropath 210 is formed between the glass substrate 207 and an opposite substrate. In this case, as shown in FIG. 3A, in the neighborhood of the silver nanoparticles fixed on the glass substrate 207, the micropath 210 may desirably be configured to have a smaller width (thickness) thereof.

Next, detection of an antigen-antibody reaction is performed by using the above prepared localized plasmon resonance sensor apparatus in the following manner.

First, a change in refractive index in the neighborhood of the surface of the group of silver nanoparticles due to the antigen-antibody reaction is measured by detecting a change in absorption spectrum. More specifically, as shown in FIG. 3A, the incident light 203 from the light source 201 is caused to enter a portion at which the group of shell-structured silver nanoparticles is fixed in a direction different from an extension direction of the micropath 210, and the reflected light 203 or transmitted light is detected by the light detector 204 to effect measurement. The light source 201 may preferably have a source wavelength of approximately 3.0 μm (infrared light) to approximately 300 nm (ultraviolet light) at which the light does not transmit through the glass substrate 207. The source wavelength may further preferably be in a range, from approximately 1.7 μm and approximately 2.5 μm, permitting measurement of both a resonance peak causing a red shift and a resonance peak causing a blue shift. However, in the case of using infrared light with a wavelength in a range from 1.4 μm to 2.6 μm as the incident light from the light source, there is large absorption by water. For this reason, it is desirable that the adverse affect by water is removed by effecting optical measurement with the reflected light or with a micropath having a thickness of not more than several μm.

In the micropath (reaction path), a specimen is caused to flow so that it comes in contact with the group of silver nanoparticles surface-modified with the antibody to effect measurement (detection) of the reflected light or the transmitted light by means of the light detector. By detecting any of or a combination of a plurality of the first change to the fifth change of absorption spectra as specifically described in the analysis embodiment, confirmation of an occurrence of the antigen-antibody reaction is effected.

According to this embodiment, the silver film thickness of the silver nanoparticles is set in the neighborhood of a value allowing the presence of the degeneracy area, so that it is possible to realize a localized plasmon resonance sensor with high sensitivity. Further, by using the localized plasmon resonance sensor in combination with a microchip, it is possible to utilize the combination thereof as a small and high-performance microanalyzing system for analyzing a chemical substance and protein.

According to the present invention, as described hereinabove, it is possible to realize a localized plasmon resonance sensor capable of high-sensitivity detection by improving the SN ratio of the localized plasmon resonance sensor.

While the invention has been described with reference to the structures disclosed herein, it is not confined to the details set forth and this application is intended to cover such modifications or changes as may come within the purpose of the improvements or the scope of the following claims.

This application claims priority from Japanese Patent Application No. 161853/2005 filed Jun. 1, 2005, which is hereby incorporated by reference.

What is claimed is:

1. A sensing method for detecting a change in an optical constant in an ambient solvent of a nanostructure comprising metal and being capable of localized plasmon resonance, said method comprising:
   detecting the change in the optical constant by detecting a change in each of a pair of plasmon resonance peaks in a response spectrum with respect to light incident on said nanostructure,
   wherein one of said pair of plasmon resonance peaks is shifted to a longer wavelength side by the change in the optical constant in the ambient solvent and the other of said pair of plasmon resonance peaks is shifted to a shorter wavelength side by the change in the optical constant in the ambient solvent,
   wherein at least one of said pair of plasmon resonance peaks is shifted to the shorter wavelength side when a dielectric constant of the ambient solvent is increased and is shifted to the longer wavelength side when the dielectric constant of the ambient solvent is decreased.

2. A method according to claim 1, wherein said nanostructure has a localized plasmon resonance frequency $\omega_{LPR}$ which, in quasi-electrostatic field approximation, is represented by the following quadratic equation with respect to the complex dielectric constant $\epsilon_{metal}(\omega_{LPR})$ of said metal contained in said nanostructure:

$$\epsilon^2_{metal}(\omega_{LPR}) + 2\alpha\epsilon_{metal}(\omega_{LPR}) + \beta = 0$$

and the coefficients $\alpha$ and $\beta$ satisfy the following relationship:

$$0 < \sqrt{\alpha^2 - \beta} \ll 1.$$

3. The method according to claim 2, wherein said nanostructure is a multi-layer shell structure comprising metal.

4. The method according to any one of claims 1 to 3, wherein the optical constant is any one of a refractive index, a dielectric constant, a magnet permeability, and combinations of these.

5. The method according to any one of claims 1 to 3, wherein the change in optical constant is caused by any one of a chemical reaction, a physical interaction, an antigen-antibody reaction, a change in temperature, and combinations of these.

6. The method according to any one of claims 1 to 3, wherein the response spectrum is any one of a transmission spectrum, a reflection spectrum, a quenching spectrum, a scattering spectrum, and an absorption spectrum.

7. The method according to any one of claims 1 to 3, wherein said nanostructure is disposed in a path in which a fluid is moved.

8. A method according to claim 7, wherein said nanostructure is disposed in a neighborhood of an area in which a width of the path is narrowed in the path.

9. The method according to any one of claims 1 to 3, wherein the ambient of said nanostructure is modified with an antigen or an antibody at a peripheral portion of said nanostructure.

10. A localized plasmon resonance sensor for detecting a change in optical constant of an ambient solvent by using a structure comprising a dielectric material as a core coated with metal as a shell, wherein in a response spectrum with respect to light incident on said structure, there are at least two resonance peaks including at least one resonance peak shifted to a longer wavelength side by the change in optical constant of the ambient solvent and at least another peak shifted to a shorter wavelength side by the change in optical constant of the ambient solvent, and wherein at least one of said at least two resonance peaks is shifted to the shorter wavelength side when a dielectric constant of the ambient solvent is increased and is shifted to the longer wavelength side when the dielectric constant of the ambient solvent is decreased.

11. A sensor according to claim 10, wherein said structure having at least two interfaces between the metal and the dielectric material and localized plasmon resonances at respective interfaces are correlated with each other.

12. A sensor according to claim 10, wherein said structure has a localized plasmon resonance frequency which includes two coefficients $\alpha$ and $\beta$ and is determined by a quadratic equation, with respect to complex dielectric constant of metal contained in said structure, represented by the following equation:

$$\epsilon^2_{metal} + 2\alpha\epsilon_{metal} + \beta = 0$$

and the coefficients $\alpha$ and $\beta$ satisfying the following relationship:

$$0 < \sqrt{\alpha^2 - \beta} \ll 1.$$

13. A method according to claim 1, wherein said pair of plasmon resonance peaks includes a shorter wavelength side peak shifted to the longer wavelength side and includes a longer wavelength side peak shifted to the shorter wavelength side.

14. A sensor according to claim 10, wherein the at least two resonance peaks includes a shorter wavelength side peak shifted to the longer wavelength side and includes a longer wavelength side peak shifted to the shorter wavelength side.

\* \* \* \* \*